US011352599B2

United States Patent
Maischberger et al.

(10) Patent No.: US 11,352,599 B2
(45) Date of Patent: Jun. 7, 2022

(54) CONCENTRATION MEASURING DEVICE FOR A CONTAINER WITH AN ESSENTIALLY LIQUID CONTAINER CONTENT

(71) Applicant: ZETA GmbH, Lieboch (AT)

(72) Inventors: Thomas Maischberger, St. Paul im Lavantal (AT); Florian Krainer, Graz (AT)

(73) Assignee: ZETA GmbH, Lieboch (AT)

( * ) Notice: Subject to any disclaimer, the term of this patent is extended or adjusted under 35 U.S.C. 154(b) by 0 days.

(21) Appl. No.: 16/761,576

(22) PCT Filed: Mar. 4, 2019

(86) PCT No.: PCT/AT2019/060069
§ 371 (c)(1),
(2) Date: May 5, 2020

(87) PCT Pub. No.: WO2019/169416
PCT Pub. Date: Dec. 12, 2019

(65) Prior Publication Data
US 2020/0270562 A1    Aug. 27, 2020

(30) Foreign Application Priority Data
Mar. 6, 2018    (AT) .............................. A 50182/2018

(51) Int. Cl.
*C12M 1/34*    (2006.01)
*C12M 1/06*    (2006.01)
*C12M 1/26*    (2006.01)

(52) U.S. Cl.
CPC ............ *C12M 41/30* (2013.01); *C12M 27/02* (2013.01); *C12M 33/14* (2013.01); *C12M 41/26* (2013.01); *C12M 41/34* (2013.01)

(58) Field of Classification Search
CPC ...... C12M 41/30; C12M 41/26; C12M 41/34; C12M 27/02; C12M 33/14
(Continued)

(56) References Cited

U.S. PATENT DOCUMENTS 4,683,207 A * 7/1987 Waarvik ............... B01D 61/147
422/552
4,695,551 A    9/1987 Sambaber et al.
(Continued)

FOREIGN PATENT DOCUMENTS

DE    35 16 080 A1    11/1986
DE    198 48 542 A1    5/2000
(Continued)

OTHER PUBLICATIONS

Int'l Search Rep and Written Opinion of the Int'l Searching Auth for Int'l Pat Appln No. PCT/AT2019/060069 dated Jun. 3, 2019, 14 pgs.

*Primary Examiner* — Michael L Hobbs
*Assistant Examiner* — Lenora A Abel
(74) *Attorney, Agent, or Firm* — Merchant & Gould P.C.

(57) ABSTRACT

A measuring device for a container having a process connection for determining the concentration of a constituent in an essentially liquid container content, comprising a concentration sensor, wherein the measuring device comprises a filter, an extraction line and a pump, wherein the filter is arranged within the container and the concentration sensor is arranged outside of the container, and the extraction line runs, starting from the filter, through the process connection to the concentration sensor, with the concentration sensor being connected to the pump, and the pump conveys the container content from the container through the filter across the extraction line to the concentration sensor, with the extraction line having at least one bend located between the filter and the process connection.

16 Claims, 1 Drawing Sheet

(58) Field of Classification Search
USPC .................................................. 435/287.5
See application file for complete search history.

(56) References Cited

U.S. PATENT DOCUMENTS

| | | | |
|---|---|---|---|
| 5,834,657 A | 11/1998 | Clawson et al. | |
| 6,544,424 B1* | 4/2003 | Shevitz | C12M 47/10 |
| | | | 210/650 |
| 7,875,448 B2* | 1/2011 | Furey | C12M 29/16 |
| | | | 435/289.1 |
| 8,753,871 B2* | 6/2014 | West | G05D 21/02 |
| | | | 435/286.1 |
| 2013/0081995 A1* | 4/2013 | Larsen | C12M 25/16 |
| | | | 210/443 |

FOREIGN PATENT DOCUMENTS

| | | |
|---|---|---|
| DE | 11 2004 002 636 T5 | 12/2006 |
| DE | 10 2009 037 345 A1 | 12/2010 |
| EP | 0 184 441 A2 | 6/1986 |
| FR | 2 617 286 A1 | 12/1988 |

\* cited by examiner

CONCENTRATION MEASURING DEVICE FOR A CONTAINER WITH AN ESSENTIALLY LIQUID CONTAINER CONTENT

This application is a National Stage Application of PCT/AT2019/060069, filed 4 Mar. 2019, which claims benefit of Serial No. A 50182/2018, filed 6 Mar. 2018 in Austria, and which applications are incorporated herein by reference. To the extent appropriate, a claim of priority is made to each of the above-disclosed applications.

BACKGROUND

Measuring device for a container having a process connection for determining the concentration of a constituent in an essentially liquid container content, comprising a concentration sensor.

Furthermore, the invention relates to a measuring method for determining the concentration of a constituent in an essentially liquid container content of a container.

Containers for receiving an essentially liquid container content and comprising a process connection are used in many industrial sectors, such as, for example, in the food industry or in the biopharmaceutical industry. Often, a biological process takes place in those containers, in which case such containers are referred to as bioreactors. The best possible conditions for the growth and product formation of microorganisms cultivated therein as well as plant, animal, insect or human cells are to be provided in bioreactors. Such conditions include optimal temperature, pH milieu, osmolarity, nutrient supply (substrate and oxygen), the discharge of metabolites and $CO_2$ and local heat sources as well as a low tendency toward stratification due to excessive density differences (e.g. sedimentation). Those homogeneous conditions are achieved in bioreactors via a suitable geometry of the container, via fittings and agitators provided therein and comprising stirring elements for mixing the contents of the container, as well as via optimal process parameters such as, for example, a rotational speed of the agitator, optimal gassing rates as well as an optimal gas discharge and nutrient addition. One of the most important parameters for the description of the performance and the homogeneity or, respectively, the mixing quality of a bioreactor is the gas/liquid mass transport, since, especially in aerobic processes, oxygen is usually the limiting substrate for the growth of microorganisms. The concentration of various constituents in the container content is of interest also for containers with essentially liquid container contents in other industrial sectors.

Oxygen is one of the most important substrates in a bioprocess. For a characterization of a process proceeding in a bioreactor, among other things, a mathematical determination of the mass transport from the gas phase into the liquid phase using various calculation approaches is applied. A stirring activity of the agitator and a turbulence of the container content generated thereby, a container geometry and a gas bubble size related thereto as well as rise heights of the gas bubbles, a gas input and a media system in the bioreactor are considered in those approaches.

Measurements for determining the concentration of constituents in the container contents of bioreactors are carried out according to the prior art via a local measurement in the bioreactor. Various measuring systems available on the market are, for example, able to determine the oxygen content dissolved in the liquid phase of the container content. Measuring systems are also known which perform a gas balancing by determining the gas input and the gas output.

In large-volume bioreactors, the main problem that arises is that the container content is inhomogeneous. Microorganisms usually react very sensitively to small fluctuations both in temperature and in nutrient, oxygen and metabolite concentrations. Such inhomogeneities, concentration, temperature and oxygen content gradients in large bioreactors arise, among other things, via gassing units, the geometry of the substrate addition, the process parameters and the stirring elements of the agitator. The interplay between the individual conditions results in zones with excess nutrient supply and areas with a strongly reduced oxygen content in the bioreactor, usually in the upper area and close to the ground. In particular, the anaerobic zones not only reduce productivity, but also promote an irreversible production of undesirable by-products.

Measuring devices according to the prior art determine concentrations of constituents in the container via standard sensors on nozzles welded into the container. DE 11 2004 002 636 T5, for example, discloses a bioreactor with an oxygen sensor arranged on a container wall. Such measuring devices according to the prior art have the disadvantage that they provide no possibility of generating information with a satisfactory spatial resolution about the distribution of oxygen in the container content. A particular disadvantage is that all measuring methods available on the market for determining the gas content and the gas transport have the common feature that measurements in the interior of the bioreactor or of the container, respectively, are always a localized recording the position of which must be precisely defined already during the planning of the process and the design of the container. By contrast, a measurement using input and output values produces only an averaged image about the total volume of the container and does not allow any conclusions to be drawn about local distributions and inhomogeneities resulting therefrom.

Measuring devices available on the market include concentration sensors with different response times. Concentration sensors with prolonged response times generally provide more precise values in the upper measuring range, close to a maximum saturation, with a concentration sensor having a shorter response time usually operating more accurately in the measuring range of low concentration values. However, all measuring devices on the market for determining the concentration of constituents in the container content have the disadvantage that gas bubbles flowing past the concentration sensor have a very strong influence on the respective measured value and cause a strong fluctuation in the measured value. As a result, it becomes necessary to use concentration sensors with longer reaction times of up to one minute in order to reduce this effect. However, this results in a shift in the measured value toward higher concentration values, since the current measured value is averaged because of the inertia of the concentration sensor. In addition, the diffusion from a gas bubble across a membrane of the concentration sensor into a measuring chamber of the concentration sensor proceeds much faster than a diffusion from the liquid phase. Moreover, most measuring devices use a mathematical averaging of the measured values in order to further reduce those fluctuations in measured values. Nevertheless, gas bubbles that flow past the concentration sensors influence the averaged measured values to a considerable extent.

SUMMARY OF THE INVENTION

It is the object of the present invention to build a measuring device for determining the concentration of a constituent in an essentially liquid container content, which avoids the disadvantages of the prior art.

According to the invention, the present object is achieved in that the measuring device comprises a filter, an extraction line and a pump, wherein the filter is arranged within the container and the concentration sensor is arranged outside of the container, and the extraction line runs, starting from the filter, through the process connection to the concentration sensor, with the concentration sensor being connected to the pump, and the pump conveys the container content from the container through the filter across the extraction line to the concentration sensor, with the extraction line having at least one bend located between the filter and the process connection.

The measuring device according to the invention is integrable into a container having a process connection and a stirring tool.

The present object of the invention is furthermore achieved by a measuring method for determining the concentration of a constituent in an essentially liquid container content of a container by means of a measuring device according to the invention, characterized by the steps of:
a) conveying a container content from the container through the filter via the extraction line to the concentration sensor by the pump;
b) determining the concentration of the constituent in the container content conveyed to the concentration sensor by the concentration sensor.

The measuring device according to the invention for a container having a process connection for determining the oxygen content of an essentially liquid container content comprises a concentration sensor, a filter, an extraction line and a pump. The filter is arranged within the container, and the concentration sensor is arranged outside of the container. Starting from the filter, the extraction line runs through the process connection of the container to the concentration sensor. The concentration sensor is connected to the pump. The pump conveys the container content from the container through the filter via the extraction line to the concentration sensor. Subsequently, the concentration sensor determines the oxygen content of the container content conveyed to the concentration sensor. To determine the oxygen content of the container content, the measuring device according to the invention removes a small amount of container content from the container by means of the extraction line. In doing so, the container content is sucked through the filter by the pump, whereby gaseous oxygen, in the form of gas bubbles, is deposited on the filter. In this way, the advantage is obtained that the gas bubbles have no influence on the measurement process and are not able to affect the measuring result. It is particularly advantageous that, because of this, no mathematical averaging of the measured values is necessary, provided that this was used in the prior art for smoothing fluctuating measured values in a specific application. Furthermore, the advantage is thereby obtained that different concentration sensors can be used which, for example due to their low mechanical stability, are not suitable for use in the interior of the container or would produce excessive measuring errors in the presence of gas bubbles in the container content. This enables the use of concentration sensors with reaction times of less than one second, as a result of which a high temporal resolution of the oxygen content measurement can advantageously be provided. Another advantage of the measuring device according to the invention is that both new and existing containers, or, respectively, bioreactors, are equipped with the measuring device according to the invention which can operate in a sterile manner and is cleanable and sterilizable.

BRIEF DESCRIPTION OF THE DRAWINGS

Advantageous embodiments of the device according to the invention and of the method according to the invention and of alternative embodiment variants are explained in further detail below with reference to the figures.

DETAILED DESCRIPTION

Figure 1:
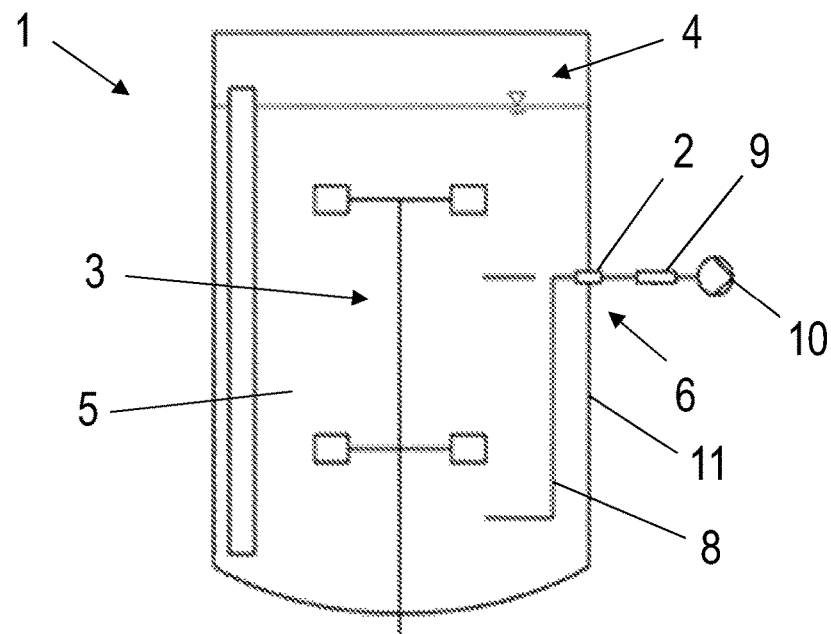
FIG. 1 shows a container comprising a measuring device according to the invention in a schematic cross-sectional view.
Figure 2:
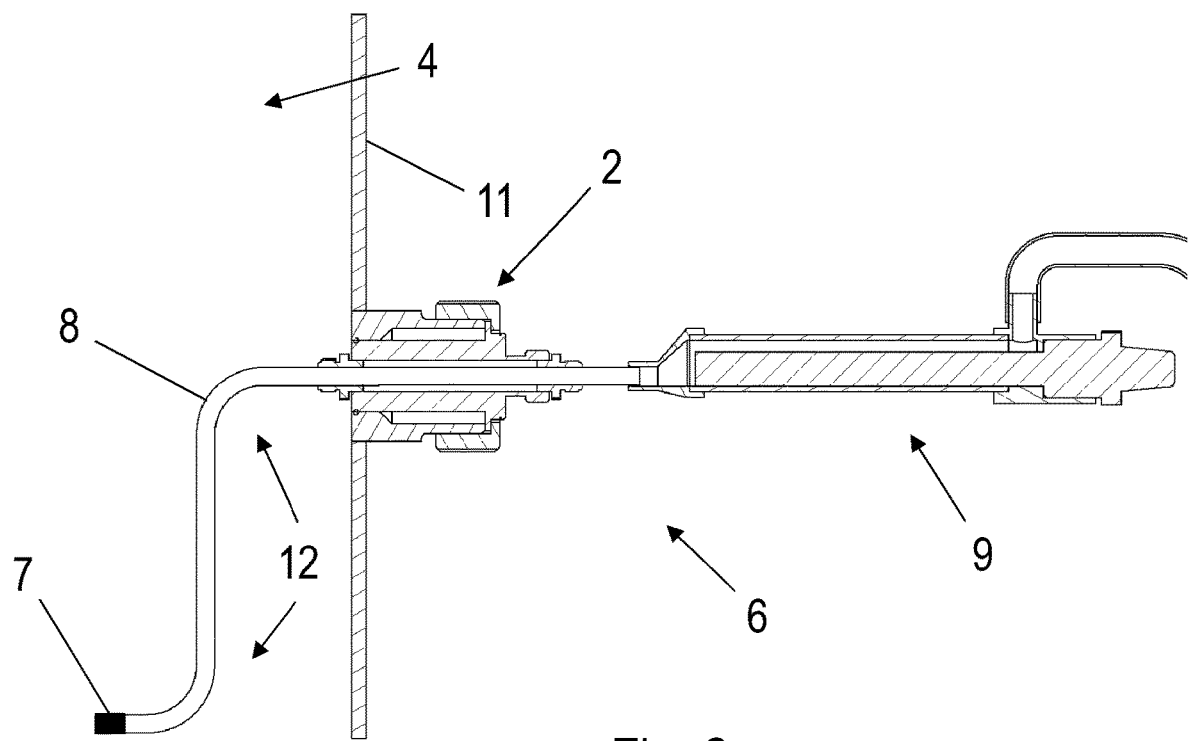
FIG. 2 shows the measuring device according to the invention of FIG. 1 with a conduct through a process connection of the container.

FIG. 1 shows a container 1 comprising a process connection 2 and a stirring tool 3, which is arranged in an interior 4 of the container 1, in a schematic view. An essentially liquid container content 5 is accommodated in the interior 4 of the container 3. The stirring tool 3 is driven from outside of the container 1 and performs a rotational movement, as a result of which mixing of the container content 5 is effected. Furthermore, the container 1 has a measuring device 6 for determining the concentration of a constituent in the container content 5. The measuring device 6 comprises a filter 7, which is illustrated in FIG. 2, an extraction line 8, a concentration sensor 9 and a pump 10. The filter 7 is arranged in the interior 4 of the container 1, and the concentration sensor 9 is arranged outside of the container 1. Starting from the filter 7, the extraction line 8 runs through the process connection 2 of the container 1 to the concentration sensor 9. The extraction line 8 leads through the process connection 2 and passes therein through a wall 11 of the container 1. The extraction line 8 is sealed in the process connection 2 by means of a threaded clamp. The concentration sensor 9 is connected to the pump 10, with the pump 10 conveying the container content 5 from the interior 4 of the container 1 through the filter 7 and the extraction line 8 to the concentration sensor 9 in the course of a measurement process. The concentration sensor 9 determines the concentration of the constituent of the container content 5. A constituent present in a gaseous state, such as, for example, oxygen or $CO_2$ in the form of gas bubbles located in the container content 5, is deposited on the filter 7 in the interior 4 of the container 1. In this way, the advantage is obtained that no gaseous constituent reaches the concentration sensor 9 outside of the container 1 via the extraction line 8. It is particularly advantageous that, in this manner, a higher measuring accuracy compared to measuring devices according to the prior art is achieved. Another advantage is that, as a result, it becomes possible to use concentration sensors 9 with a short response time, for example of less than one second, in the measuring device 6 according to the invention, whereby small concentration differences and changes are detectable with the measuring device 6 according to the invention. Furthermore, the measuring device 6 according to the invention does not require a mathematical smoothing of the measured values. According to the preferred embodiment of the measuring device 6, the pump 10 is designed as a peristaltic pump. In this way, the advantage is obtained that the container content 5 in the extraction line 8 is conveyed continuously and essentially without pressure fluctuations to the concentration sensor 9.

FIG. 2 shows the measuring device 6 shown in FIG. 1 in a sectional view with the filter 7, the extraction line 8 and the concentration sensor 9 in a preferred embodiment. The pump 10 is not illustrated in FIG. 2. Furthermore, the process connection 2 of the container 1 with the extraction line 8 guided through the latter, as well as a section of the wall 11 of the container 1 are illustrated. The extraction line 8 exhibits two bends 12, which are arranged between the filter 7 and the process connection 2. In an alternative embodiment variant of the measuring device 6, the extraction line 8 has at least one bend 12. Due to the bend 12, the advantage is achieved that the extraction line 8 is adaptable to the geometry of the interior 4 of the container 1 and to the geometry of the stirring tools 3 exemplified in FIG. 1. It is particularly advantageous that, in this way, different removal positions for the container content 5, which is not shown in FIG. 2, can be achieved in the interior 4 of the container 1, if the standardized process connection 2 is used. A further advantage is that, unlike with measuring devices according to the prior art, the concentration of the constituent in the container content can be determined at different freely selectable measuring positions in the interior 4 of the container 1 by means of only one concentration sensor 9.

According to the preferred embodiment of the measuring device 6, the extraction line 8 is rotatably mounted in the process connection 2. In this way, the advantage is obtained that, in combination with the curved extraction line 8, a variety of different removal positions can be reached. It is particularly advantageous that, by rotating the extraction line 8, for example, a concentration profile in the container content along a height of the container 1 can thereby be detected by means of the measuring device 6 according to the invention. According to the preferred embodiment of the measuring device 6, the extraction line 8 is furthermore displaceably mounted in the process connection 2. In this way, the advantage is obtained that the removal position can also be varied in the radial direction of the container 1 or, respectively, in a container depth. This creates further possibilities for the establishment of concentration profiles. By appropriately adjusting the bend 12 or the bends 12 of the extraction line 8, collisions of the extraction line 8 with the stirring tools 3 in the container interior 4 are avoided. In this way, the advantage is obtained that measurements can be performed with the measuring device 6 according to the invention also during the operation of the stirring tool(s) 3.

According to the preferred embodiment of the measuring device 6 according to the invention, the concentration sensor 9 is a flow sensor. In this way, the advantage is obtained that a continuous measurement of the concentration can be provided and that mathematical interpolation calculations are avoided during the establishment of a concentration profile of the constituent of the container content 5 from individual measuring points. The concentration sensor 9 preferably has a reaction time of less than one second. In this way, the advantage is obtained that even small fluctuations in the concentration are reliably detected. The flow sensor sets the container content 5 into a turbulent flow. The turbulent flow is generated, for example, with a series of protrusions in a flow passage of the flow sensor. Further possibilities for generating a turbulent flow result from this exemplary reference for a person skilled in the art. In this way, the advantage is obtained that a separation of gaseous constituents dissolved in the container content 5 from the liquid phase into the gaseous phase is avoided in the flow sensor. According to the preferred embodiment, the measuring device 6 furthermore has a return line, which is not depicted in the figures. The return line is connected to the pump 10 and the container 1. The integration of the return line has the advantage that a container content 5 removed from the container 1 is returned into the container 1. It is particularly advantageous that a measurement of the concentration with the measuring device 6 according to the invention will thus not lead to a depletion of the container content 5.

According to the preferred embodiment variant of the measuring device 6 according to the invention, the filter 7 is a cloth screen. In particular, the filter 7 is a metal cloth screen. In this way, the advantage is obtained that the surface of the filter 7 has a low flow resistance to liquids and, at the same time, is not passable for gas bubbles. The metal cloth screen preferably consists of a stainless steel material with a material quality which corresponds to that of the container 1. In addition, the cloth screen is cleanable, sterilizable and autoclavable, respectively.

According to an embodiment variant of the measuring device 6 according to the invention, the concentration sensor 9 is a gas content sensor, such as an oxygen content sensor or a $CO_2$ content sensor, or a pH value sensor. In this way, the advantage is obtained that various parameters of the container content can be detected by means of the device according to the invention.

The measuring device 6 according to the invention is integrable directly into the container 1 as described under FIG. 1, which comprises the process connection 2 and the stirring tool 3. The process connection 2 is preferably a tri-clamp (TC) connection or an ingold connection. Additional process connections 2 result for the person skilled in the art from this exemplary reference. In this way, the advantage is obtained that the measuring device 6 according to the invention can be integrated in containers 1 with process connections 2 customary in the market.

With the measuring device 6 according to the invention, a method for determining the concentration of the constituent in the essentially liquid container content 5 of a container 1 equipped with the measuring device 6 according to the invention is carried out. For determining the concentration, a container content 5 is conveyed from the container 1 through the filter 7 via the extraction line 8 to the concentration sensor 9 by means of the pump 10 in a first procedural step. Subsequently, the concentration of the constituent in the container content 5 conveyed to the concentration sensor 9 is determined by means of the concentration sensor 9. In this way, the advantage is obtained that gas bubbles possibly present in the container content 5 are deposited on the filter 7 rather than being conveyed to the concentration sensor 9.

According to the preferred embodiment of the method according to the invention, the extraction line 8 is rotated and/or shifted in the process connection 2 while the container content 5 is conveyed from the container 1 through the filter 7 via the extraction line 8 to the concentration sensor 9. In this way, the advantage is obtained that a concentration profile of the constituent in the container content 5 is established both across various height layers of the container 1 and/or toward a container centre.

The device according to the invention and the method according to the invention for determining the concentration of the constituent in the essentially liquid container content 5 are equally suitable for determining further physical and/or chemical parameters of the container content 5. In this connection, the concentration sensor 9 is replaced by a sensor sensitive to the parameter to be determined.

It is particularly advantageous to design the geometry and the displaceability and rotatability of the extraction line 8 such that a collision with the rotating agitator 3 is reliably avoided. Hence, a person conducting the measurement does not have to be afraid of damaging the filter 7 or the agitator 3 if the oxygen content is to be measured while the agitator 3 is mixing the liquid container content 5.

It may be mentioned that the configuration of the liquid container content can be from runny to viscous and mushy.

The invention claimed is:

1. A measuring device for a container having a process connection for determining the concentration of a constituent in an liquid container content, the measuring device comprising:
   a concentration sensor;
   a filter;
   an extraction line; and
   a pump,
      wherein the filter is configured to be arranged within the container and the concentration sensor is configured to be arranged outside of the container, and the extraction line runs, starting from the filter, through the process connection to the concentration sensor, with the concentration sensor being connected to the pump, and the pump conveys the liquid container content from the container through the filter across the extraction line to the concentration sensor, with the extraction line having at least one bend located between the filter and the process connection.

2. The measuring device according to claim 1, wherein the extraction line is rotatably mounted in the process connection.

3. The measuring device according to claim 1, wherein the extraction line is displaceably mounted in the process connection.

4. The measuring device according to claim 1, wherein the concentration sensor is a flow sensor.

5. The measuring device according to claim 4, wherein the flow sensor is designed for setting the liquid container content into a turbulent flow.

6. The measuring device according to claim 1, wherein the pump is a peristaltic pump.

7. The measuring device according to claim 1, wherein the measuring device has a return line, with the return line being connected to the pump and the container.

8. The measuring device according to claim 1, wherein the filter is a cloth screen.

9. The measuring device according to claim 8, wherein the cloth screen is a metal cloth screen.

10. The measuring device according to claim 1, wherein the concentration sensor has a reaction time of less than one second.

11. The measuring device according to claim 1, wherein the concentration sensor is a gas content sensor or a pH value sensor.

12. The measuring device according to claim 1, wherein the concentration sensor is an oxygen content sensor or a $CO_2$ content sensor.

13. The measuring device according to claim 1, wherein the container further comprises a stirring tool.

14. The measuring device according to claim 13, wherein the process connection is a tri-clamp (TC) connection or an ingold connection.

15. A measuring method for determining the concentration of a constituent in an liquid container content of a container, the measuring method comprising:
   conveying a container content from the container through a filter, the filter being configured to be arranged within the container, via an extraction line to a concentration sensor, the concentration sensor being configured to be arranged outside the container, by a pump, wherein the extraction line pass through a process connection in the container; and
   determining the concentration of the constituent in the liquid container content conveyed to the concentration sensor with the concentration sensor,
   wherein the extraction line includes at least one bend located between the filter and the process connection.

16. The measuring method according to claim 15, wherein conveying the container content further comprises at least one of:
   (1) rotating the extraction line in the process connection, and
   (2) shifting the extraction line in the process connection.

* * * * *